(12) United States Patent
Van Der Burg et al.

(10) Patent No.: US 8,821,575 B2
(45) Date of Patent: *Sep. 2, 2014

(54) METHODS AND DEVICES FOR RHINOPLASTY AND TREATING INTERNAL VALVE STENOSIS

(75) Inventors: Erik Van Der Burg, Los Gatos, CA (US); Michael Dineen, Portola Valley, CA (US); Mark Hirotsuka, San Jose, CA (US); Jasper Jackson, Newark, CA (US); Andrew Frazier, Sunnyvale, CA (US); Chad Roue, San Jose, CA (US)

(73) Assignee: Koninklijke Philips N.V., Eindhoven (NL)

( * ) Notice: Subject to any disclaimer, the term of this patent is extended or adjusted under 35 U.S.C. 154(b) by 17 days.

This patent is subject to a terminal disclaimer.

(21) Appl. No.: 13/235,773

(22) Filed: Sep. 19, 2011

(65) Prior Publication Data

US 2012/0041556 A1 Feb. 16, 2012

Related U.S. Application Data

(62) Division of application No. 11/770,471, filed on Jun. 28, 2007, now Pat. No. 8,038,712.

(51) Int. Cl.
*A61F 2/18* (2006.01)
*A61M 29/00* (2006.01)
*A61F 5/08* (2006.01)
*A61F 2/28* (2006.01)

(52) U.S. Cl.
CPC . *A61F 2/186* (2013.01); *A61F 5/08* (2013.01); *A61F 2002/2885* (2013.01)
USPC .............................. 623/10; 606/196; 606/199

(58) Field of Classification Search
CPC .... A61F 5/08; A61F 2/186; A61F 2002/2885
See application file for complete search history.

(56) References Cited

U.S. PATENT DOCUMENTS

| | | | |
|---|---|---|---|
| 1,481,581 A | 1/1924 | Woodward | |
| 1,597,331 A | 8/1926 | Thurston | |
| 4,105,035 A | * 8/1978 | Rella | 606/199 |
| 4,414,977 A | 11/1983 | Rezakhany | |
| 5,350,396 A | 9/1994 | Eliachar | |

(Continued)

FOREIGN PATENT DOCUMENTS

| | | |
|---|---|---|
| WO | 03003930 A1 | 1/2003 |
| WO | 2008003097 A2 | 1/2008 |

OTHER PUBLICATIONS

Friedman, M.D., Michael, "Nasal Valve Suspension: An Improved, Simplified Technique for Nasal Valve Collapse" Laryngoscope 113, Jan. 2003, pp. 381-385.

(Continued)

*Primary Examiner* — David H Willse
*Assistant Examiner* — Javier Blanco

(57) ABSTRACT

Methods and devices for rhinoplasty and treating nasal valve stenosis are disclosed herein. The nasal valve acts as a flow-limiter and can contribute to airway obstruction if resistance within the nasal valve is excessive. In one embodiment, a system for treating nasal valve stenosis includes a first elongate implant and a second elongate implant configured to support the nasal valves when implanted. The implants can be coupled together by connecting elements, such as eyelets, tethers, complementary socket joints, and button-rivet supports.

5 Claims, 8 Drawing Sheets

(56) References Cited

U.S. PATENT DOCUMENTS

| | | | |
|---|---|---|---|
| 5,554,194 A * | 9/1996 | Sanders | 623/17.17 |
| 5,599,284 A * | 2/1997 | Shea | 602/17 |
| 5,816,241 A | 10/1998 | Cook | |
| 6,106,541 A | 8/2000 | Hurbis | |
| 6,270,512 B1 | 8/2001 | Rittmann | |
| 6,322,590 B1 | 11/2001 | Sillers | |
| 2002/0173848 A1 | 11/2002 | Sachs | |
| 2004/0059368 A1 * | 3/2004 | Maryanka | 606/191 |
| 2004/0064083 A1 | 4/2004 | Becker | |
| 2004/0078054 A1 | 4/2004 | Biggs | |
| 2004/0261791 A1 | 12/2004 | Horian | |
| 2006/0207608 A1 | 9/2006 | Hirotsuka | |
| 2006/0276817 A1 | 12/2006 | Vassallo | |

OTHER PUBLICATIONS

Nunez-Fernandez M.D., David "Rhinoplasty, Internal Valve Stenosis" May 2007. Emedicine.

* cited by examiner

METHODS AND DEVICES FOR RHINOPLASTY AND TREATING INTERNAL VALVE STENOSIS

REFERENCE TO RELATED APPLICATIONS

This application claims priority under 35 U.S.C. §119(e) to U.S. Provisional Application No. 60/817,565 filed Jun. 29, 2006 and No. 60/875,067 filed Dec. 15, 2006. Both of the priority applications are hereby incorporated by reference in their entirety.

BACKGROUND OF THE INVENTION

1. Field of the Invention

Embodiments of the present invention disclose devices and methods for treating the collapse of structures within the nose that form the passageways for airflow during inhalation.

2. Description of the Related Art

The airflow resistance provided by the airways during breathing is essential for good pulmonary function. The nose is responsible for almost two thirds of this resistance. Most of this resistance occurs in the anterior part of the nose. This region is called the nasal valve, and it acts as a flow-limiter.

The nasal valve was originally described by Mink in 1903. It is divided into external and internal portions. The external nasal valve is formed by the columella, the nasal floor, and the nasal rim (or caudal border of the lower lateral cartilage). The nasalis muscle dilates this portion during inspiration. The internal nasal valve accounts for the larger part of the nasal resistance. It is located in the area of transition between the skin and respiratory epithelium, and it is usually the narrowest part of the nose. The internal nasal valve is the better-known valve and is often referred to as the nasal valve.

The two terms should be differentiated because the internal nasal valve or "nasal valve" accounts only for the aperture between the nasal septum and the caudal border of the upper lateral cartilage (ULC). The angle formed between them is normally between about 10°-15°.

The nasal valve area is formed by the nasal septum, the caudal border of the ULC, the head of the inferior turbinate, and the pyriform aperture and the tissues that surround it. This area is responsible for more than two thirds of the resistance produced by the nose.

In 1894, Franke performed nasal-flow experiments in models and cadavers and found that whirl formation occurred near the head of the turbinate during calm breathing. The term nasal valve was first coined by Mink in 1903. He developed this concept further in 1920, suggesting that the greatest area of resistance was in the limen nasi or the union of the lobular cartilage and ULCs.

In 1940, Uddstromer found that 70% of the resistance of the nose was produced in the nasal valve area and the remaining 30% was due to the nasal fossa. Van Dishoeck further investigated the mechanisms of the nasal valve in 1942, and in 1970, Bridger and Proctor wrote about a "flow-limiting segment" that included the limen nasi and the pyriform aperture. In 1972, Bachman and Legler found the pyriform aperture to have the smallest cross-sectional area of the nasal airway.

In 1983, Haight and Cole continued the study of Bridger and Proctor and demonstrated that the maximal nasal resistance was localized near the pyriform aperture and depended on engorgement of the head of the inferior turbinate.

As many as 13% of the patients with chronic nasal obstruction have nasal valve collapse. Of these patients, 88% have unilateral collapse.

External nasal valve collapse is often found in patients who do not have a history of trauma or surgery. These patients commonly have an overprojecting nose with extremely narrow nostrils. Another cause can be an extremely wide columella.

Types of internal nasal valve collapse can be differentiated depending on the structure that caused the collapse. In many cases, more than one structure is affected. The most common cause is probably septal deviation. The second cause is collapse secondary to rhinologic surgery, especially after removal of the nasal roof.

In 1987, Kasperbauer and Kern developed a comprehensive classification; however, the classification below depends on the anatomical area.

Deviations of the caudal septum are the most common cause of valvular collapse. They are usually secondary to trauma. The septum can be overly thick in the valvular area, decreasing the space in it. Also, an absence of cartilage in this area leaves a flaccid septum that moves during inspiration.

Thickened cartilage can compromise an adequate aperture. The cartilage can also be twisted, deflected, or associated with excessive return of the caudal border. An absence of cartilage, either congenital or iatrogenic, can produce a flaccid valve that collapses during inspiration.

Overresection during rhinoplasty can weaken the cartilage and cause inspiratory collapse. Deformation of the cartilage can be a result of trauma or congenital malformations of the cartilage.

Trauma or previous surgery can create webs or stenosis in the valvular area. The tissue can also be too thick, reducing the lumen of the valve. This can be a result of inflammation or hypertrophy.

Hypertrophy of the inferior turbinate can significantly increase nasal resistance. Several studies have demonstrated that the head of the turbinate is responsible for most of this increase. In comparison, the body and tail of the turbinate play minor roles in nasal resistance. The increase in size can be secondary only to mucosa or bone hypertrophy.

Although uncommon, some patients may have deformities of the pyriform aperture that reduce the space of the nasal valve. The first description the authors found of a congenital stenosis of the pyriform aperture was made by Brown et al in 1988; other reports have followed, such as Ramadan, 1995; Fornelli, 2000; and Lee, 2002. A more common cause of obstruction is the osteotomy made during a rhinoplasty. In particular, the type known as low-to-low is blamed for excessive narrowing of the pyriform aperture. Some modifications to this procedure allow an osteotomy to be performed without compromising the space in the valve.

Rhinoplastic procedures are particularly prone to disturbing the nasal valve area. Hump removal affects the nasal valve in several ways. If the hump is particularly large, separation of the ULC can be necessary. Resection of the T-shaped area of the dorsal border of the septum produces a narrower area in the roof. If the mucosa in the valve is not protected during the surgery, which occurred with the use of many older techniques, scarring of the valve can lead to structure formation or stenosis of the valve. In reduction rhinoplasties, the cross-sectional area of the overall nose is reduced. This increases the resistance to airflow. If the nasal valve is not properly repaired during the surgery, patients may report nasal obstruction after the surgery, even if this was not reported preoperatively. Overresection of the lower lateral cartilage can lead to pinching and inspiratory collapse.

Age is another factor to consider. The relaxation of tissues may eventually produce a flaccid valve. In these cases, surgery of the valve can correct the loss of patency.

The internal nasal valve works as a flow-limiting area. The fixed part of the valve is composed of the septum and the pyriform aperture. The ULC and the mucosa of the turbinate act as the mobile part. When air is inspired, it is forced through this narrow area, increasing its speed and pressure. Just after passing the valve, the air expands in the bony cavum, creating turbulence that promotes contact between the air and the mucosa. In this way, the inspired air is cleansed of particles, humidified, and heated or cooled (depending on its temperature).

Because it is the narrowest part of the nose, the nasal valve can be affected by minute alterations of the nasal anatomy that would not be important in other areas. The angle between the ULC and the nasal septum is typically between about 10°-15°. Internal nasal valve collapse occurs when, for some reason, this angle is diminished. The result is an increase in nasal resistance to airflow; consequently, the patient reports nasal obstruction. The opposite is known as ballooning. In this case, the nasal valve is excessively open.

The increase in nasal resistance is also related to abnormalities of pulmonary function. These changes in pulmonary function return to normal after septal surgery is performed and nasal resistance is decreased.

Patients primarily report nasal obstruction. Other symptoms are crusting and bleeding, but these are more often associated with septal deviation.

Diagnosis can be difficult if the physician does not visualize the valvular area. Examining the valve without disturbing it with a nasal speculum is important because the speculum usually opens the valve. Sometimes, trimming the vibrissae is necessary to obtain a clearer view of the valve. Another method is to use a 0° endoscope.

The Cottle test is useful to evaluate nasal valve stenosis. The cheek of the evaluated side is gently pulled laterally with 1-2 fingers, which opens the valve. The examiner then asks the patient to breathe and evaluates if breathing is better before or after pulling the cheek. A positive test result is when the patient feels less resistance with the valve opened. This test is easy and quick to perform.

The internal nasal valve is limited medially by the nasal septum. Laterally, in its superior part, it is limited by the caudal border of the ULC, where it forms the limen nasi with the cephalic border of the lobular cartilage. The angle between the septum and the ULC is generally between about 10°-15° in patients of Caucasian descent. Patients of other ethnic backgrounds can demonstrate great variability in this septum-ULC angle measurement. In this area, epithelium shifts from the skin of the vestibule to the respiratory mucosa of the bony cavum.

The pyriform aperture continues the limit of the valve from the ULC to the floor. The head of the inferior turbinate is immediately posterior to the pyriform aperture and plays an important role in the function of the valve, which is the reason it is also considered part of the internal nasal valve. In some patients, particularly white persons, the caudal border of the ULC scrolls externally in what is called the returning of the ULC. When this returning is excessive, it can produce valve collapse.

In addition to the typical reasons to avoid surgery (e.g., bleeding disorders), other contraindications include excessive scarring due to multiple previous surgeries, which may compromise the outcome of the procedure, the presence of cheloid scarring, and unrealistic patient expectations.

Imaging studies such as CT scanning of paranasal sinuses can be performed to, for example, obtain coronal views which can provide good information on the patency of the nasal valve, especially the area under the nasal dorsum (nasal valve area), which is sometimes difficult to visualize. However, these studies are expensive and should not be considered a substitute for comprehensive physical examinations.

Other diagnostic tests that can performed include rhinomanometry and acoustic rhinometry. Rhinomanometry aids in evaluating the airflow resistance offered by each cavity but does not provide information about the location of the obstruction. Acoustic rhinometry is relatively new, as it was introduced in the late 1980s, and it can provide information about the cross-sectional area of the nose and about the position of obstructions. Results from the anterior portion of the nose tend to be more accurate than results from the posterior portion, making this test particularly suitable for evaluating the valve. Acoustic rhinometry can be used to evaluate the symmetry of nasal areas.

The nasal valve is better explored without instruments because tools can open the valve and produce the false impression that the area is normal. A headlight and an endoscope are the only necessary instruments to examine the nasal valve. In many male patients (and some females), the vibrissae are thick, making direct visualization of the area difficult. If this occurs, one option is to trim them until the valve can be visualized.

The Cottle test is a good method to examine the vestibular portion of the nasal valve. It consists of pulling the nasolabial fold upward and laterally and asking the patient if breathing is better. An affirmative answer implies that a collapse of the valve is present on that side. A negative answer means the cause of the obstruction is elsewhere in the nose. A false-positive result can occur in patients with collapse of the nasal ala. False-negative results are observed in patients with scars or webs in the valve that prevent it from opening. False-negative results also occur in those with narrowing of the pyriform aperture secondary to congenital malformation or after an excessive narrowing of the nasal base with an osteotomy.

When the valvular collapse is secondary to inflammation of the mucosa covering the valve (e.g., secondary to allergic rhinitis or infection), proper treatment, such as anti-inflammatory agents or antibiotics, can help remedy the problem.

Collapse secondary to mechanical obstruction is more common. In this case, surgery is the only solution. Some patients use a self-adhesive stent that opens the nasal valve; however, this is only a temporary solution.

Several surgical techniques are used to correct a stenotic or collapsed nasal valve. Depending on the type of pathology, the surgeon can choose to use one or several methods. The scope of techniques varies from sutures to the application of grafts. The common goal is to open the valve, restoring the appropriate anatomy. Explaining each technique is beyond the scope of this article; however the following is a summary of these techniques depending on the structure modified.

A valvuloplasty is the surgery historically used to reconstruct the nasal valve. The goal of this surgery is to open the valve by removing the returning ULC and trimming the caudal border of the cartilage. It is not the only technique used to correct valvular alterations, but it provides an excellent view of the caudal border of the ULC and can be used in conjunction with other techniques. Because the valve is formed by several different structures, other techniques may be necessary, depending on the type of deformity that produced the stenosis.

The goal of this procedure is to expose the caudal border of the ULC to correct any deformity (e.g., resection of the caudal border of the ULC, excessive returning of the ULC). The following preliminary steps can be taken when performing this procedure: expose the caudal border of the ULC through an intercartilaginous incision, avoid damaging the valvular mucosa in order to decrease the risk of a synechia, and place intercartilaginous incisions 1-2 mm caudal to the border of the ULC. The area of transition from skin to respiratory epithelium is prone to developing unwanted scarring or synechiae. Then the following steps can be taken:

Undermine the skin over the dorsum.

To obtain better exposure, gently retract the alar margin of the nostril with a 10- or 12-mm double hook.

Grasp the caudal border of the ULC with an Adson-Brown or similar forceps.

Dissect the mucosa in the underside of the ULC with the tip of a Walter or curved Iris scissors.

Similarly separate the upper side of the ULC from the subcutaneous tissue until the caudal border is completely visible.

Repeat the same procedure if the dorsum is visible from both sides.

Almost any deformity of the ULC can be identified this way.

If a septoplasty or rhinoseptoplasty was performed and the caudal border of the septum was resected, resect a similar amount of the caudal border of the ULC. This maintains the proportions between the septum and the ULC.

Resection of the caudal border of the ULC reduces its flexibility. To maintain it, removing a small triangle near the septum may be necessary.

If another deformity is present, direct surgery to correct it. For example, if the ULC is twisted, a batten may be necessary to straighten it.

Spreader grafts can be inserted and fixed through this incision to increase the cross-sectional area of the nose.

When intercartilaginous incisions do not allow enough space to see and work because of the complexity of the stenosis, an open approach provides excellent exposure (i.e., when spreader grafts and flaring sutures are applied in the same procedure).

A dry field is important in this surgery because the space is limited and bleeding can obstruct the visual field and make the procedure time consuming. To avoid this, the cul-de-sac can be infiltrated 5-10 minutes prior to the incision. Apply only a small amount of lidocaine and epinephrine (Octocaine with epinephrine [2%], Xylocaine with epinephrine [2%]). Approximately 0.5 mL is needed in each valve to avoid distortion of the structures. Help from an assistant is invaluable.

Suturing of the intercartilaginous incision is performed at the end of the surgery, when all other maneuvers have been completed. Some prefer to use catgut or 4-0 Vicryl with ophthalmic needles. These small curved needles are easy to handle in the confined space of the vestibule.

Normal preoperative examinations can be performed, and no special care is required. The surgery is often performed in combination with septoplasty or rhinoseptoplasty. Local or general anesthesia can be used.

Because the valve is formed by several structures, the surgery is directed toward realigning the obstructing parts.

If a caudal deviation is causing the obstruction, a septoplasty can correct the problem. Septoplasty is a difficult surgery because caudal deviations are commonly complex deformities of the septal framework and obtaining a completely straight septum proves to be a frustrating task. In some cases, obtaining straight cartilage from the posterior septum and transplanting it is preferable. This is particularly true in those patients with horizontal fractures of the caudal septum (e.g., Chevallet fractures). The use of battens is sometimes necessary to keep the repaired septum straight.

The nasal roof can be excessively narrowed after rhinoplasty or with congenital or traumatic deformities. In these cases, the use of spreader grafts, as described by Sheen in 1984, is particularly useful. They keep the nasal profile straight, and they also increase the cross-sectional area of the entire nasal valve.

If the cartilage is thick or if excessive returning of the caudal border of the cartilage occurs, modification is possible by resecting the caudal border and reshaping the valve. This is commonly a surgery performed concomitantly with septoplasty. Also, the previously mentioned spreader grafts can modify the position of the cartilage, allowing the valve to open. In case the cartilage is absent, a graft can be fashioned from septal or auricular cartilage. Another method described to open the nasal valve is to apply a flaring suture that lifts the ULCs. A combination of both techniques has recently been reported to have the best results. The ULC can be sutured using several different techniques, including suspension sutures (Lee, 2001) and mattress sutures (Ozturan, 2002).

When the alar cartilage is weakened after surgical overresection or trauma, its rigidity must be restored. The basic method consists of applying a batten of cartilage to keep the lobule rigid during inspiration. A method described by O'Halloran in 2003 consists of the removal of excessive skin in the valvular area through an incision anterior to the LLC.

Although complete resection of the turbinate is best avoided, conservative resection (or manicuring) of the head of the turbinate significantly decreases the total resistance offered by the internal valve. This procedure, when performed properly, is a useful tool when the other areas are difficult to correct. Unless hypertrophy is extremely large, resecting more than 2 cm from the head typically is not necessary because the airflow follows a superior direction afterwards.

Narrow pyriform apertures should be handled depending on the origin of the constriction. Congenital pyriform stenosis can be produced from an excess of bone. This bone can be drilled away through a sublabial approach. If the stenosis was produced by an excessive narrowing of the nasal bones in a previous surgery, it can be handled with resection of a small wedge of bone in the narrowest area. Another approach is to displace the bones laterally (outfracture) after performing new osteotomies. In this case, performing medial and lateral osteotomies is recommended. If neither procedure is successful, conservative resection of the head of the inferior turbinate is an alternative plan. In many patients, more than one procedure is necessary to open the valve.

This situation is difficult to handle. Obstructive scarring is common after surgery. Resection of the synechia or scarring is performed with scissors. Because some synechia and scars are quite thick, a good method is to clamp the valve with a forceps for 5 minutes before the procedure in order to obtain better hemostasis. Good results have been obtained by separating both sides of the valve with a silicone sheet (Silastic). Because the author routinely uses silicone (Silastic) splints for septal surgery, the splint must simply be cut into a proper shape and size and then sutured to the septum with nylon 3-0 or 4-0 suture. A contralateral splint is recommended to avoid unnecessary damage to the mucosa.

Incisions can be closed with 4-0 catgut or Vicryl, preferably with ophthalmic needles to facilitate the closure. A typical dressing can be applied to the rest of the nose, depending on the surgery performed (e.g., dressing and cast for rhinoplasty).

The need for hospitalization following these types of procedures depends on the type of anesthesia used, the recovery of the patient, and the evaluation of the physician. Because the procedures are primarily performed in combination with septoplasty, the same care used following septoplasty is applicable for these procedures.

Thus, there remains an unmet need in the art for non-traumatic, non-surgical treatments for the collapse of structures within the nose that form the passageways for airflow.

SUMMARY OF THE INVENTION

In some embodiments, disclosed herein is a system for supporting a nasal valve. The system can include a first elongate implant configured to support a first nasal valve; a second elongate implant configured to support a second nasal valve; and means for connecting the first elongate implant to the second elongate implant. The means for connecting the first elongate implant to the second elongate implant can include complementary socket joints on the first elongate implant and the second elongate implant. In other embodiments, the means for connecting the first elongate implant to the second elongate implant include an eyelet located on the first elongate implant and an eyelet located on the second elongate implant, and a tether for connecting the eyelets. In other embodiments, the means for connecting the first elongate implant to the second elongate implant include an eyelet located on the first elongate implant and a split eyelet located on the second elongate implant. In still other embodiments, the means for connecting the first elongate implant to the second elongate implant can include an interlocking button-rivet support.

Also disclosed herein is a system for supporting a nasal valve, including a first elongate implant that includes a first connecting element; and a second elongate implant that includes a second connecting element. The first connecting element and the second connecting element are configured to be operably connected to each other such that the system supports a nasal valve. In some embodiments, the first connecting element includes a male socket joint and the second connecting element includes a female socket joint configured to be coupled to the male socket joint. In some embodiments, at least one of the first connecting element and the second connecting element includes an eyelet. In some embodiments, the first connecting member includes a first eyelet and the second connecting member includes a second eyelet. The system also preferably includes an elongate member configured to pass through the first eyelet and the second eyelet to secure the first elongate member to the second elongate member. The elongate member can be, for example, a rivet, a tether, or the like.

A method of supporting a nasal valve is also disclosed. The method includes the steps of providing a first elongate implant; inserting the first elongate implant to a first position adjacent a first nasal valve to support the first nasal valve; providing a second elongate implant; and inserting the second elongate implant to a second position adjacent a second nasal valve to support the second nasal valve. Inserting the first elongate implant can include creating an access pathway near the nasal bridge. The method can also include connecting the first elongate implant to the second elongate implant.

Connecting the first elongate implant to the second elongate implant can involve securing a portion of the first elongate implant and the second elongate implant together using a tether. Securing a portion of the first elongate implant and the second elongate implant together using a tether can include threading the tether through an eyelet located on the first elongate implant and an eyelet located on the second elongate implant. In other embodiments, connecting the first elongate implant to the second elongate implant involves threading a split eyelet located on the second elongate implant through a solid eyelet located on the first elongate implant, and securing the split eyelet to the solid eyelet. In other embodiments, connecting the first elongate implant to the second elongate implant involves connecting a socket portion of the first elongate implant to a complementary socket portion of the second elongate implant. In still other embodiments, connecting the first elongate implant to the second elongate implant includes passing an elongate rod through an aperture on the first elongate implant and an aperture on the second elongate implant.

Also disclosed is a method of suspending a nasal valve, including the steps of providing a delivery cannula, the cannula comprising a nasal suspension assembly housed within a working lumen of the cannula, the nasal suspension assembly comprising a tissue anchor and a tether operably connected to the tissue anchor; creating an incision on a facial region of a patient; passing the delivery cannula through the incision in proximity to the orbital rim; retracting the delivery cannula to expose the tissue anchor and the tether; deploying the first anchor within a tissue layer within a lateral wall of a nasal passage; and securing the tether near the orbital rim to support the nasal valve. The facial region of a patient can be, for example, in proximity to the infraorbital rim. In some embodiments, the method further includes the step of passing the delivery cannula through a nostril of the patient prior to passing the delivery cannula through the incision. In some embodiments, the delivery cannula includes a curved distal tip portion. The tissue anchor can include a tissue-ingrowth surface. The tissue anchor can also be an expandable tissue anchor. The tissue layer can be, for example, mucosa, cartilage, dermis, or subcutaneous fascia. Securing the tether line can involve securing the tether line to a bony structure, or alternatively, to soft tissue.

Also disclosed is a method of suspending a nasal valve, including the steps of providing a nasal suspension system comprising a first tissue anchor, a second tissue anchor, and a tether operably connected to the first tissue anchor and the second tissue anchor; deploying the first tissue anchor within a first soft tissue layer within a wall of a nasal passage; deploying the second tissue anchor within a second soft tissue layer; and tensioning the tether to suspend the nasal valve. Tensioning of the tether to suspend the nasal valve can occurs prior to, after, or concurrently with deploying the second tissue anchor within the second soft tissue layer. In some embodiments, the method also includes the steps of providing a delivery cannula, the cannula including the nasal suspension system housed within a working lumen of the cannula; passing the delivery cannula through a nostril to a desired location to suspend the nasal valve; and retracting the delivery cannula to expose the nasal suspension system. The second tissue layer can be in any clinically desirable location, such as, for example, in the vicinity of the infraorbital rim. The second tissue layer can be, for example, the mucosa, cartilage, dermis, or subcutaneous fascia. In some embodiments, the first tissue anchor and the second tissue anchor are expandable tissue anchors. In some embodiments, the delivery cannula includes a curved distal tip portion. In some embodiments, the method also includes the step of adjusting the tension of the nasal suspension system after deployment of the system. Adjusting the tension of the nasal suspension system after deployment of the system can be accomplished by an adjustment element disposed along a portion of the nasal suspension system.

Also disclosed is a kit for suspending the nasal valve, including: a nasal suspension system configured to support a nasal valve once implanted, the nasal suspension system comprising: a first tissue anchor; a second tissue anchor; an elongate member configured to be connected to the first tissue anchor and the second tissue anchor; and a delivery cannula configured to house the nasal suspension system within a working channel of the delivery cannula. At least one of the first tissue anchor and second tissue anchor can be expandable tissue anchors. Furthermore, at least one of the first tissue anchor and second tissue anchor can include a tissue in-growth surface. The delivery cannula can include a curved distal portion.

In some embodiments, disclosed is a system for suspending a nasal valve, including: a first tissue anchor configured to be attached to a lateral wall of a nasal passage; and an elongate member configured to be attached to the first tissue anchor and the second tissue anchor, the elongate member also configured to suspend a nasal valve. The system can also include a second tissue anchor configured to be attached to another structure on a facial region. The first tissue anchor can be an expandable tissue anchor. The first tissue anchor can also include a tissue ingrowth surface. In some embodiments, the system also includes an adjustment element configured to adjust the tension of the elongate member. The adjustment element can be configured to adjust a tension of the elongate member while the elongate member is connected to the first tissue anchor and the second tissue anchor.

DETAILED DESCRIPTION OF PREFERRED EMBODIMENTS

Nasal Suspension

Figure 1A:
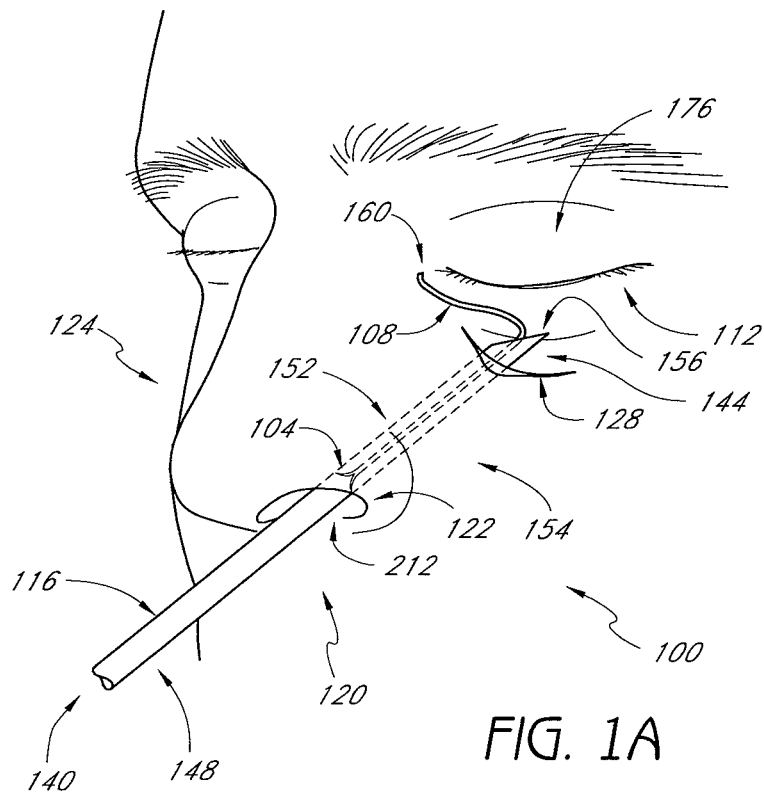
FIG. 1A shows a nasal suspension assembly being deployed through the nostrils using a cannula containing a tether line and collapsed anchor at the proximal end of the tether line, according to one embodiment of the invention.
Figure 1B:
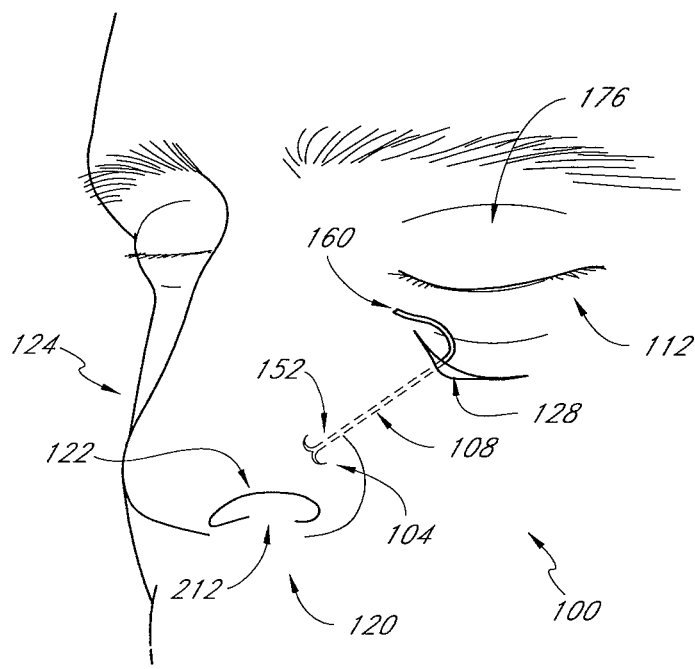
FIG. 1B shows a deployed nasal suspension assembly, after the cannula has been removed, tension has been applied to the tether line, and the anchor has been deployed, according to one embodiment of the invention.

U.S. patent application Ser. No. 11/349,067, filed Feb. 7, 2006, published as U.S. Patent Publication No. 2006/0207608 A1 on Sep. 21, 2006 and incorporated by reference in its entirety, describes methods and devices for manipulating the airway, as does U.S. Patent Publication No. 2006/0276817 to Vassallo et al., hereby incorporated by reference in its entirety, an article by David Nunez-Fernandez, M.D. et al., *Rhinoplasty, Internal Valve Stenosis*, available at www.e-medicine.com/ent/topic115.htm, and an article by Michael Friedman, M.D. et al., *Nasal Valve Suspension: An Improved, Simplified Technique for Nasal Valve Collapse*, January 2003, available at www.chicagoent.com/pdf/Nasal_Valve_Simpl.pdf. Both of the articles are hereby incorporated by reference in their entirety. In some embodiments of the present invention, collapse of structures within the nose that form the passageways for airflow is treated by deploying a nasal suspension assembly 100 within the nose 124 and thereby suspending nasal structures and opening a site of nasal collapse, such as nasal valve 122, as shown in FIGS. 1A-1B. Nasal suspension assembly 100 may comprise one or more anchors 104 and a tether line 108. Anchors 104 may be attached to mucosa, cartilage, dermis, or any connective tissue layer within the lateral walls of the nasal passages 212. Tether line 108 may be attached to the orbital rim 112 or to any structures near orbital rim 112 or between orbital rim 112 and nose 124 that are less mobile than nose 124. For example, tether line 108 can be attached to bones, periosteum, or soft tissue. Tension can subsequently be applied to tether line 108 to suspend nasal structures and thereby open the site of nasal collapse.

In one embodiment, nasal suspension assembly 100 is deployed by creating an incision 128 at the orbital rim 112 and passing a cannula 116 from the nostrils 120 of nose 124 under the surface of the skin 154 to incision 128 as shown in FIG. 1A. Cannula 116 comprises a needle tip 144 at distal end 156 and a working lumen 140 that extends from proximal end 148 of cannula 116 to distal end 156 of cannula 116. An anchor 104 is attached to the proximal end 152 of tether line 108 and tether line 108 is pre-loaded into cannula 116 by passing the tether line 108 from the proximal end 148 of cannula 116 through lumen 140 and through needle tip 144 so that the distal end 160 of tether line 108 emerges from the distal end 156 of cannula 116. Anchor 104 is retained within cannula 116 in a collapsed state. Cannula 116 is subsequently passed from nostrils 120 to incision 128, exiting incision 128 with distal end 160 of tether line 108 emerging from the surface 164 of the skin. Cannula 116 is then retracted proximally, leaving tether line 108 extending out of incision 128 as anchor 104 is released from cannula 116 and deployed within the mucosa, cartilage, dermis, or connective tissue layer within the lateral walls of the nasal passages 212, depending on the desired clinical result, in an uncollapsed state. Tension is then applied to tether line 108, for example by pulling on the end of tether line 108 extending out of incision 128. Tether line 108 is then secured so that nasal structures are suspended and the site of nasal collapse is opened as shown in FIG. 1B. Tether line can be secured with knots, crimps, clamps, adhesives, and any other mechanisms as would be understood by those skilled in the art. Incision 128 can subsequently be closed using a variety of mechanisms as would be contemplated by those skilled in the art, for example, with sutures. One advantage of deploying nasal suspension assembly 100 by introducing cannula 116 through nose 124 is that there are no facial structures near the proximal end 148 of cannula 116 that need to be avoided. In the method discussed below cannula 116 is introduced near the eye 176, and thus a curved needle tip 144 is used to avoid facial structures.

Figure 2:
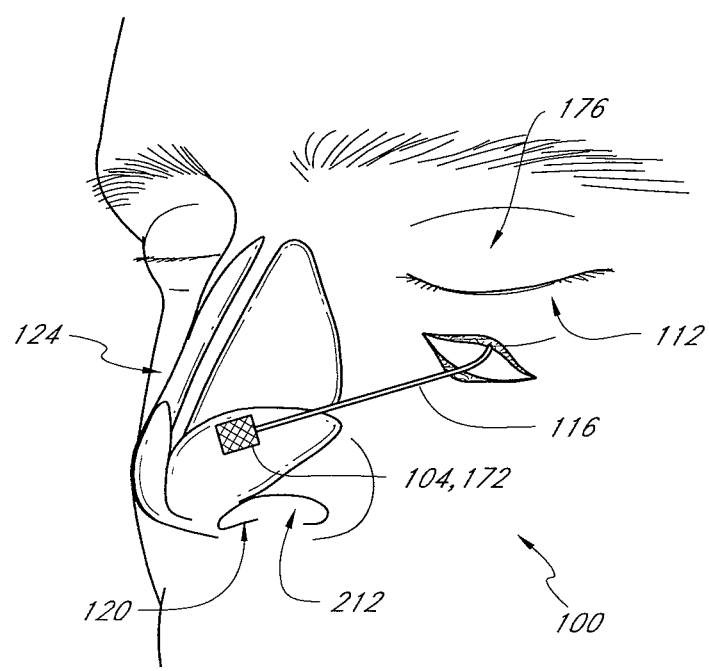
FIG. 2 shows a nasal suspension assembly being deployed in which the anchor has a tissue in-growth surface, according to one embodiment of the invention.

As shown in FIG. 2, in some embodiments anchor 104 comprises a tissue in-growth surface 172. Tissue in-growth surface 172 could enhance attachment of anchor 104 to tissue within the lateral walls of the nasal passages 212, particularly when anchor 104 has a very low profile. For example, a material that promotes tissue in-growth could cover at least a portion of the surface of anchor 104. This material could include various biocompatible materials, including ePTFE, Dacron, bioresorbable materials, polyethylene, and other materials as would be contemplated by those skilled in the art.

Figure 3:
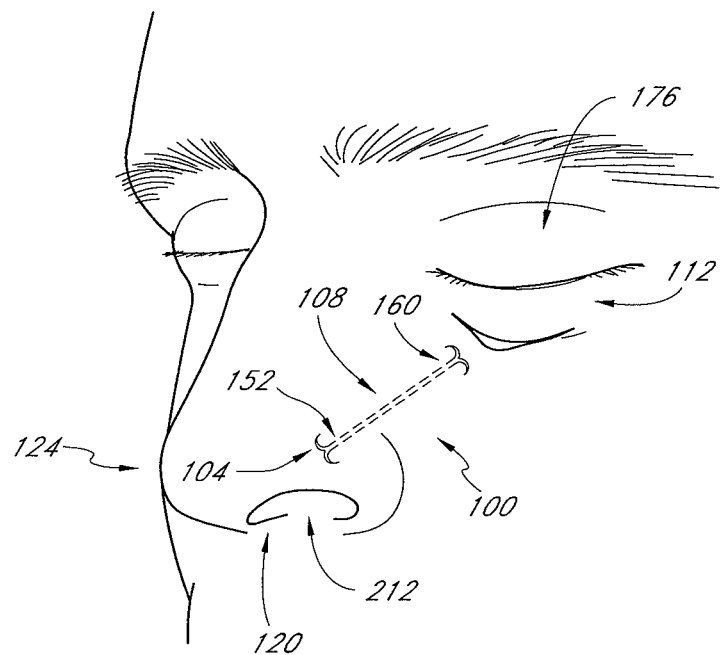
FIG. 3 shows a deployed nasal suspension assembly with anchors at both ends of the tether line, according to one embodiment of the invention.

In another embodiment, anchors 104 are placed at both proximal end 152 and distal end 160 of tether line 108, as shown in FIG. 3. Both anchors 104 are contained in a collapsed state within cannula 116. Cannula 116 is then introduced into nostrils 120 and advanced until its distal end 156 reaches an area sufficiently lateral or towards the eye, such as adjacent to orbital rim 112. Then cannula 116 is withdrawn and anchors 104 are deployed in an uncollapsed state in soft tissue thereby opening the nasal valve 122. Distal end 156 should be advanced to an area sufficiently lateral such that anchors 104 are spaced apart when deployed in the soft tissue so as to create the tension required to suspend the nasal valve 122, as shown in FIG. 3. Tension can be applied to tether line 108 either before the second anchor 104 is delivered or after both anchors 104 are delivered. In some embodiments, the length of tether line 108 between anchors 104 is fixed such that after the first anchor 104 is deployed and while the second anchor 104 still resides within cannula 116, cannula 116 is pulled to apply tension to first anchor 104 and tension line 108. In some embodiments, after both anchors 104 are deployed, tension is applied to tension line 108 by pulling on the portion of tension line 108 extending out of the distal end 156 of cannula 116. A mechanism can be employed to allow pulling of tension line 108 in the direction towards the eye only, and not in the opposite direction such that tension line 108 could be withdrawn back into cannula 116. This mechanism can comprise a lock or zip-tie or any other means disclosed in the applications and articles incorporated by reference in their entireties supra or any other means that would be contemplated by those skilled in the art. One or more of the anchors 104 may comprise a tissue in-growth surface 172. This embodiment does not require an anchor 104 or screw or other retaining means to be placed in the bone. Another advantage associated with this embodiment is that incision 128 near the eye 176 does not need to be made.

Figure 4:
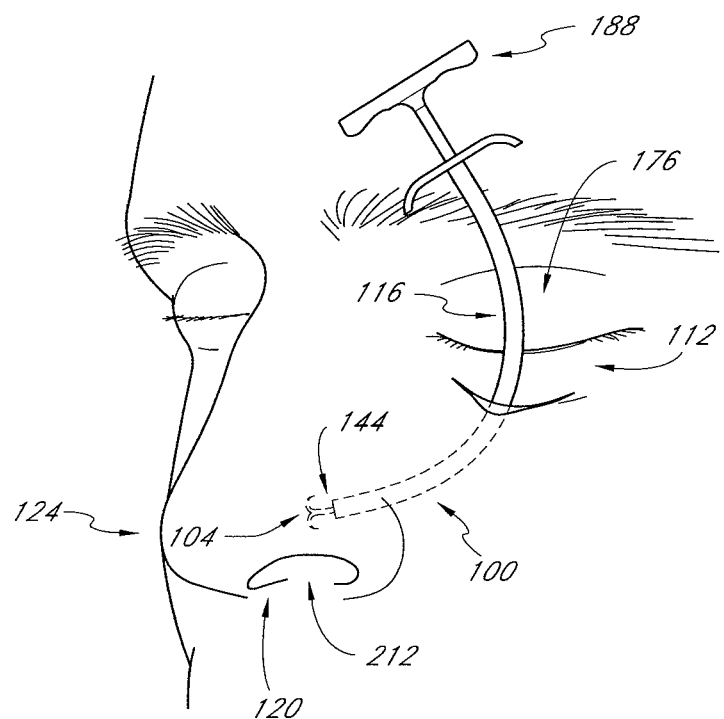
FIG. 4 shows a nasal suspension assembly being deployed from a location near the eye using a curved cannula with a plunger at its proximal end, according to one embodiment of the invention.

In yet another embodiment, as shown in FIG. 4, cannula 116 is introduced into the site of nasal collapse from near the eye 176. This method of introducing cannula 116 and subsequently deploying nasal valve suspension assembly 100 is similar to Friedman's technique which involves a transconjunctival approach that provides easy access to the infraorbital rim on patients who refuse a facial incision. (See article by Michael Friedman, M.D. et al., *Nasal Valve Suspension: An Improved, Simplified Technique for Nasal Valve Collapse*, January 2003, available at www.chicagoent.com/pdf/Nasal_Valve_Simpl.pdf, incorporated by reference in its entirety supra.) In this embodiment, cannula 116 has a curved configuration so as to avoid facial structures as described above and as shown in FIG. 4. An anchor 104 is threaded over the distal end 160 of tether line 108 and tether line 108 is passed from the proximal end 148 of cannula 116 through lumen 140. Anchor 104 is retained within cannula 116 in a collapsed state. Cannula 116 is subsequently passed from the eye to the site of nasal collapse. Plunger 188 is then actuated such that anchor 104 emerges from needle tip 144 and is deployed at the site of nasal collapse in an uncollapsed state.

Implantable Nasal Valve Support

Figure 5:
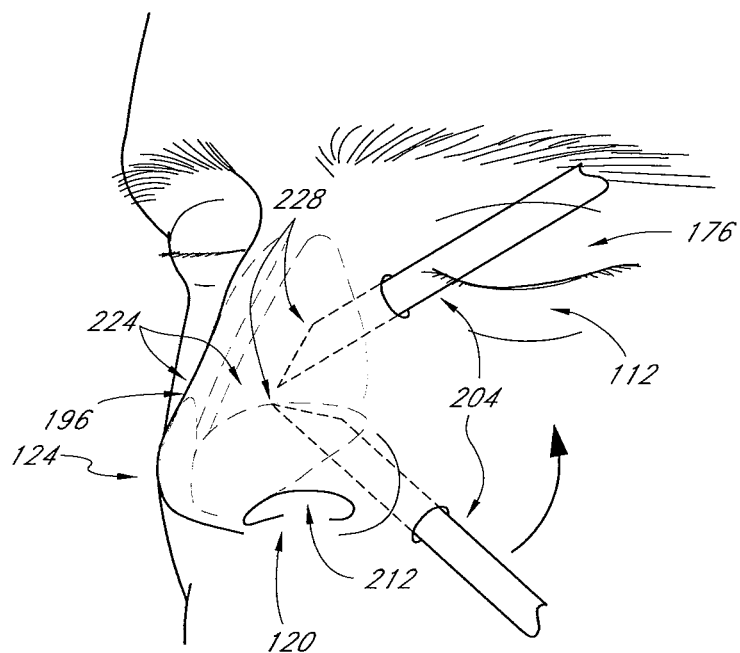
FIG. 5 shows the insertion of a needle under the surface of the nose to deploy an implant, according to one embodiment of the invention.
Figure 6:
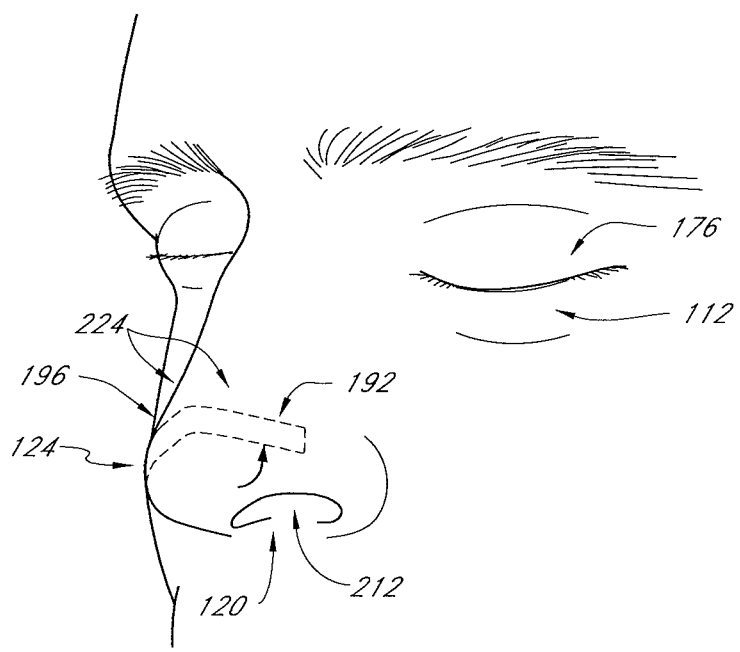
FIG. 6 shows an implant deployed across the bridge of the nose, according to one embodiment of the invention.

In another embodiment, an implant 192 can be deployed within nose 124 across the bridge 196 as shown in FIGS. 5 and 6 to open the site of nasal collapse.

In some embodiments, implant 192 is a relatively stiff elongate bar which can have a straight or bent configuration or a variety of other configurations depending on the desired clinical outcome. Implant 192 is biased when deployed to lift tissue on either side 224 of bridge 196, thereby opening the site of nasal collapse. A deployed implant 192 is depicted in FIG. 6. Implant 192 can comprise woven Dacron, ePTFE, polyethylene, or any other material as would be contemplated by those skilled in the art. Implant 192 can also be configured as a metallic strip or wire comprising Nitinol, titanium, stainless steel, or other metallic materials depending on the desired clinical outcome. In some embodiments implant 192 comprises a tissue in-growth surface 172 comprising ePTFE, Dacron, and other materials as would be contemplated by those skilled in the art. Implant 192 may also comprise a bioresorbable surface comprising materials as would be contemplated by those skilled in the art.

In one embodiment, implant 192 is delivered through a delivery needle 204 as shown in FIG. 5. Delivery needle 204 is inserted into one side 224 of nose 124 lateral to nostrils 120 and under and parallel to the surface of nose 124. As needle 204 approaches bridge 196 it is angled to run parallel to the contralateral side 224 of nose 124. In some embodiments, bridge 196 is manually depressed and/or the nares are manually elevated to assist in angling of needle 204. Needle 204 is advanced to contralateral side 224 and then retracted while implant 192 is simultaneously extruded from needle tip 228. Implant 192 is thereby deployed across bridge 196 as shown in FIG. 6 and lifts tissue on either side 224 of bridge 196 to open the site of nasal collapse. This lifting of tissue is similar to the effect obtained with a BREATHE-RIGHT® strip (Johnson & Johnson).

Two-Piece Nasal Valve Splints

In some embodiments minimally invasive implantation of nasal valve supports is facilitated by use of a two-piece splint design. Each piece of the two-piece design is inserted adjacent to one of the nasal valves through a small hole on the surface of the nose. After each piece is inserted, the two pieces are attached to obtain a configuration that supports the nasal valves. In some embodiments, the hole should preferably be at or near the bridge of the nose to provide a straight line-of-sight access path for the insertion needle/cannula into the nose along the nasal valve. Implantation of each piece separately prior to assembly is much less invasive than implantation of the two-piece assembly because each linear piece can be inserted through a small hole.

Figure 7:
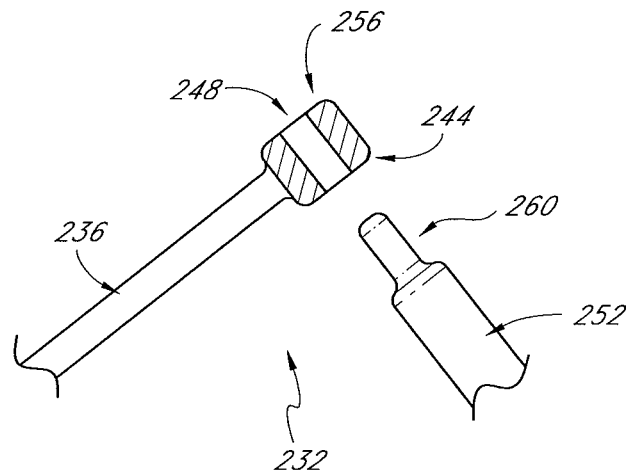
FIG. 7 shows a nasal valve implant with a two-piece splint design, according to one embodiment of the invention.

FIG. 7 shows a cross-sectional view of a "socket joint" type two-piece splint 232 comprising pieces 236 and 252. The socket end 256 of piece 236 comprises a ring-like portion 244 with a central lumen 248. Piece 252 comprises a complimentary end 260 that fits into lumen 248 of socket end 256 such that pieces 236 and 252 are locked together. Pieces 236 and 252 are implanted separately and then locked together after implantation. When assembled, splint 232 provides biasing support to prevent collapse of the nasal valves. Each splint is preferably splayed at an angle about equal to or greater than the natural angle of the nasal opening (nare). The splints serve to stabilize a weak or easily collapsible valve by stiffening it, or enlarging the existing opening which will reduce resistance and decrease the propensity for the valve to collapse. The splint can be made of a wide variety of materials as known in the art. In some embodiments, the splint is made of a silicone material if relatively less stiffening is desired. In other embodiments, the splint can be made of a metal such as titanium, stainless steel, and the like if more support or enlargement is needed and hence more stiffness. In one preferred embodiment, the splint is formed from titanium with a thin silicone covering.

Figure 8:
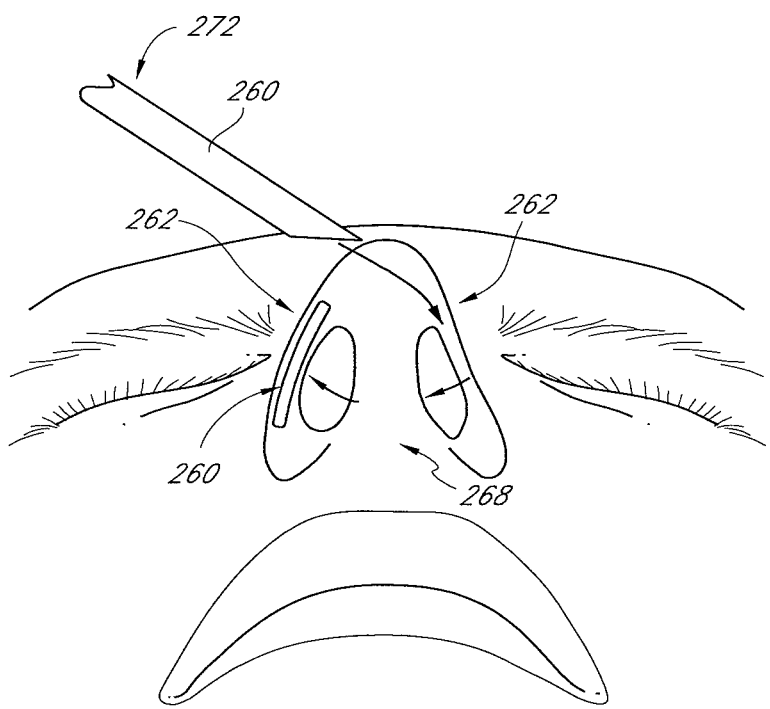
FIG. 8 shows implantation of two separate battens as a two-piece splint, according to one embodiment of the invention.

FIG. 8 shows implantation of two separate battens 260 as another two-piece nasal splint 268. As seen in FIG. 8, one batten 260 is implanted adjacent one nasal 262 valve and the second batten 260 is implanted adjacent the other nasal valve 262 to suspend each collapsing valve 262. Each batten 260 is inserted using a needle 272. The needle is then preferably removed in order to remove a potentially trauma-inducing surface. Battens 260 can be formed of materials with a desired stiffness so as to achieve suspension of the nasal valves 262 as would be understood by those skilled in the art. In some embodiments, the batten may be formed of materials that allow tissue ingrowth such as woven Dacron, porous ePTFE, and the like. If tissue ingrowth is not required or desired, for example, in cases where significant scarring and fibrosis is not desirable, silicone, solid PTFE, FEP, and the like can used to create the batten. Alternatively, the scar tissue and fibrosis that form following implantation of battens 260 can provide the necessary stiffness to achieve suspension of the nasal valves 262 either independently or in combination with the stiffness of battens 260.

Figure 9A:
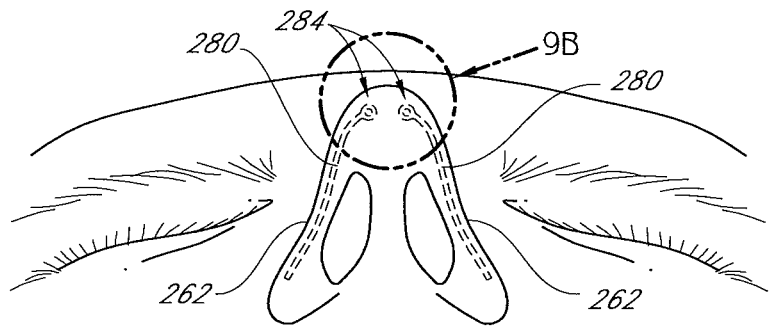
FIGS. 9A-9C show another embodiment of a two-piece nasal splint
Figure 9B:
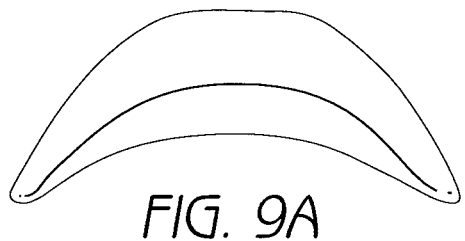
Figure 9C:
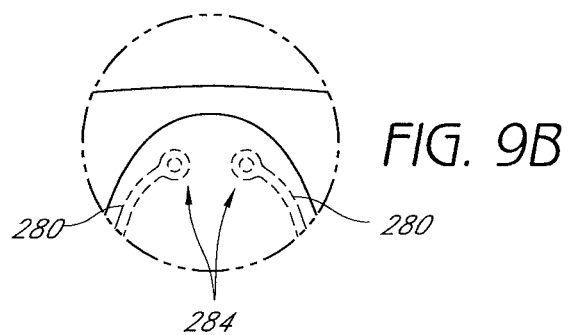
Figure 9C:
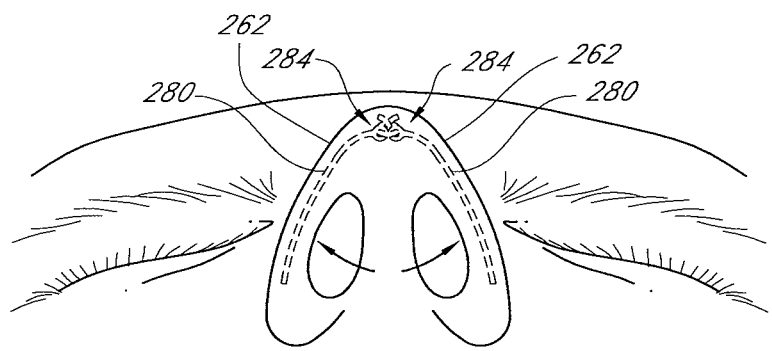

FIGS. 9A-9C show another embodiment of a two-piece nasal splint 276 which comprises two parts 280. Each part 280 comprises a head section 284 having a lumen adapted to receive suture 282. FIG. 9A shows parts 280 each placed adjacent one nasal valve 262. FIG. 9B shows head sections 284 aligned following insertion of parts 280 into the nasal valves 262. When head sections 284 are placed adjacent to each other, suture 282 can be passed through each section 284 and tied such that sections 284 are drawn tightly together as shown in FIG. 9C. When head sections 284 are aligned and tied together as shown in FIG. 9C, parts 280 of the splint are biased such that they suspend the nasal valves 262 and prevent collapse. After sections 284 are tied together, suture 282 is buried in the nasal tissue.

Figure 10A:
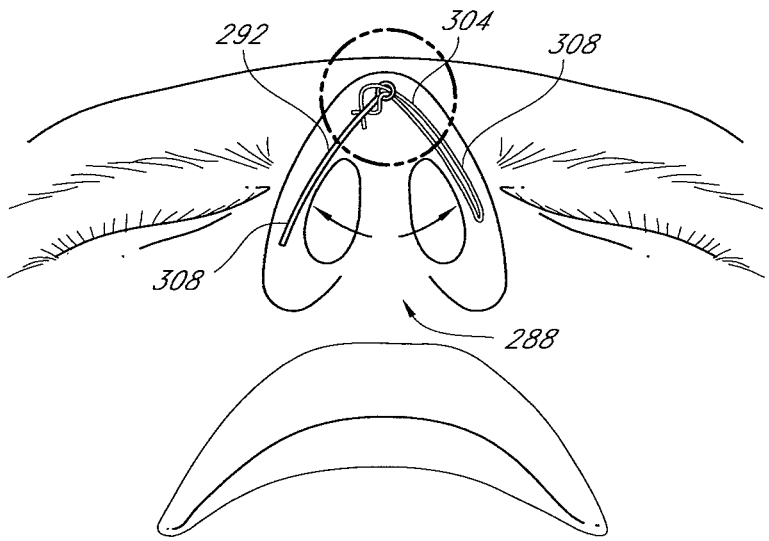
FIGS. 10A-10B show an embodiment of a two-piece nasal support.
Figure 10B:
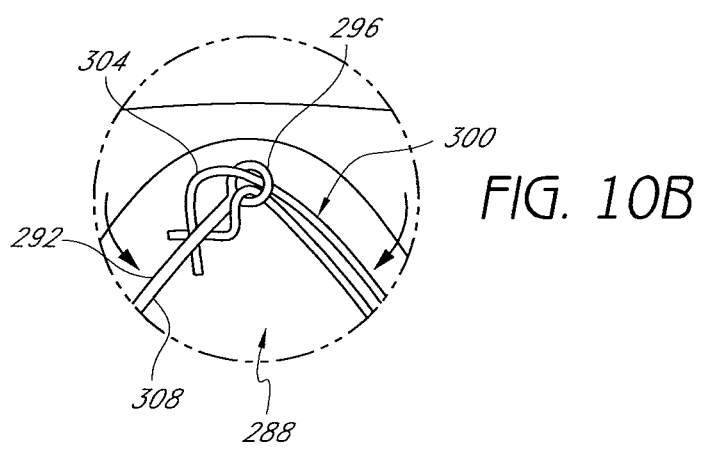

Another embodiment of a two-piece nasal support 288 is shown in FIGS. 10A-10B. Piece 292 comprises an eyelet 296 large enough to allow end 300 of second piece 304 to pass through as shown in FIG. 10B. End 300 is configured like an eyelet open at its end and split such that it may be snapped or tied over the shaft portion 308 of piece 292. Eyelet 296 and end 300 are angled with respect to the shaft portions 308 of pieces 292 and 304 as shown in FIG. 10A so as to allow angulation of shaft portions 308. The angles between eyelet 296 and end 300 and their respective shaft portions 308 can be fixed or altered as desired by the surgeon or other user at the time of implantation to obtain a customized fit. A nasal support 288 can be preferably formed from a superelastic material such as Nitinol so that it can be ejected from a needle or cannula. The wire can be formed as shown with the proximal eyelets constrained in the needle in a relatively straight configuration. An incision can be created at the bridge of the nose and a small flap created, under which the eyelets will eventually be placed. The needle is inserted along the desired axis of suspension along the margin of the nares or nasal valve and ejected from the needle. The needle is most preferably inserted deep enough to allow the eyelet of each splint to be contained underneath the tissue flap at the end of the procedure. After both splints are deployed, the split eyelet is attached to the solid eyelet. To facilitate the attachment, the physician can slide the splints slightly upward in the tract created by the needle. After the eyelets are attached, the splints are pressed back down into their respective tracts and the conjoined eyelets are buried in the incision or under the tissue flap. A pocket can be created if needed depending on the size of the eyelets and the bulk of the nose tissue available to cover the connection.

Figure 11A:
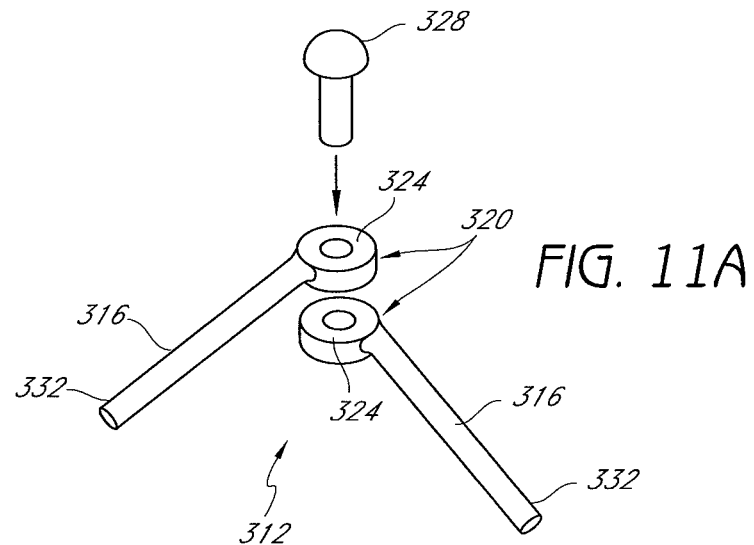
FIGS. 11A-11C show another embodiment of a two-piece nasal support.
Figure 11B:
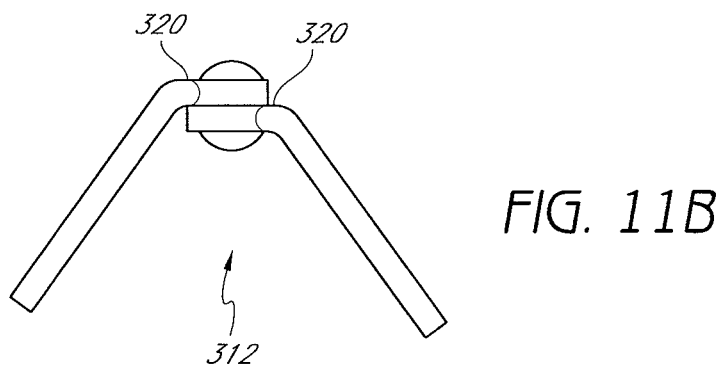
Figure 11C:
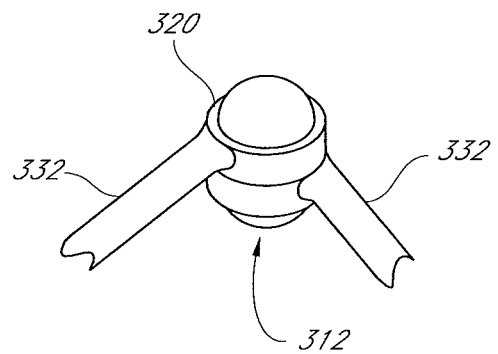

In another embodiment of a two-piece nasal support, the support is configured as a button rivet support 312 as shown in FIGS. 11A-11C. Each piece 316 of support 312 comprises a head portion 320 with a hole 324 such that when head portions 320 are placed one on top of the other and holes 324 are aligned, a rivet 328 can be passed through holes 324 to attach pieces 316 as shown in FIG. 11A. FIG. 11B is a side view of support 312 after assembly. FIG. 11C is a plan view of support 312 after assembly. Head portions 320 are angled with respect to each other to allow alignment of holes 324 and with respect to the shafts 332 of each piece 316 to create the desired valve suspension after assembly. These angles may differ for particular patients and may be modified accordingly as would be understood by those skilled in the art.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of supporting a first nasal valve and a second nasal valve of a nose of a subject, comprising:
   providing a first linear elongate implant, the first linear elongate implant having a first longitudinal axis and a first terminal end, the first terminal end having a lumen extending in a direction that is perpendicular to the first longitudinal axis;
   creating a hole on a surface of the nose near a nasal bridge of the nose;
   inserting the first linear elongate implant through the hole to a first position adjacent the first nasal valve;
   providing a second linear elongate implant, the second linear elongate implant having a second longitudinal axis and a second terminal end, the second terminal end having a complementary member extending in a direction that is parallel to the second longitudinal axis;
   inserting the second linear elongate implant through the hole to a second position adjacent the second nasal valve; and
   after the inserting steps, inserting the complementary member into the lumen to securely connect the first linear elongate implant to the second linear elongate implant and thereby providing first biasing support to the first nasal valve with the first linear elongate implant to prevent collapse of the first nasal valve and providing second biasing support to the second nasal valve with the second linear elongate implant to prevent collapse of the second nasal valve,
   wherein inserting the first linear elongate implant comprises creating the hole near a nasal bridge of the nose.

2. The method of claim 1, wherein the first linear elongate implant and the second linear elongate implant are made of a silicone material.

3. The method of claim 1, wherein the first linear elongate implant and the second linear elongate implant are made of a metal material.

4. The method of claim 1, wherein the first linear elongate implant and the second linear elongate implant are made of a metal material covered by silicone.

5. The method of claim 4, wherein the metal material is titanium.

* * * * *